United States Patent
Kobayashi et al.

(10) Patent No.: US 10,188,286 B2
(45) Date of Patent: Jan. 29, 2019

(54) TOMOGRAPHIC IMAGE CAPTURING DEVICE

(71) Applicant: KOWA COMPANY, LTD., Nagoya-shi, Aichi (JP)

(72) Inventors: Naoki Kobayashi, Higashimurayama (JP); Masaharu Mizuochi, Higashimurayama (JP); Toshiaki Nakagawa, Higashimurayama (JP)

(73) Assignee: KOWA COMPANY, LTD. (JP)

( * ) Notice: Subject to any disclaimer, the term of this patent is extended or adjusted under 35 U.S.C. 154(b) by 0 days.

(21) Appl. No.: 15/553,681

(22) PCT Filed: Feb. 26, 2016

(86) PCT No.: PCT/JP2016/055750
§ 371 (c)(1),
(2) Date: Aug. 25, 2017

(87) PCT Pub. No.: WO2016/136926
PCT Pub. Date: Sep. 1, 2016

(65) Prior Publication Data
US 2018/0008144 A1    Jan. 11, 2018

(30) Foreign Application Priority Data
Feb. 27, 2015    (JP) ................................. 2015-039325

(51) Int. Cl.
*A61B 3/10*    (2006.01)
*A61B 3/14*    (2006.01)
(Continued)

(52) U.S. Cl.
CPC ............ *A61B 3/102* (2013.01); *A61B 3/0025* (2013.01); *A61B 3/0041* (2013.01); *A61B 3/10* (2013.01);
(Continued)

(58) Field of Classification Search
CPC ......... A61B 3/102; A61B 3/14; A61B 3/0025; A61B 3/0041; A61B 3/0058;
(Continued)

(56) References Cited

U.S. PATENT DOCUMENTS

| 6,212,303 B1 | 4/2001 | Doran et al. ................... 382/245 |
| 2008/0234972 A1 | 9/2008 | Tsukada et al. ............... 702/155 |

(Continued)

FOREIGN PATENT DOCUMENTS

| CN | 102860814 | 1/2013 |
| JP | 2008237238 | 10/2008 |

(Continued)

OTHER PUBLICATIONS

Adolf Friedrich Fercher, "Optical coherence tomography—development, principles, applications", Z. Med. Phys., vol. 20, pp. 251-276, Nov. 18, 2009 (Year: 2009).*

(Continued)

*Primary Examiner* — Frank G Font
(74) *Attorney, Agent, or Firm* — Adams & Wilks

(57) ABSTRACT

The tomographic image capturing device of the present invention includes a tomographic image capturing means that scans measurement light on a subject's eye fundus (E) to capture tomographic images of the subject's eye fundus and an image processing means that compresses a picture of the captured tomographic images in a scan direction to generate a new tomographic picture. The tomographic image capturing means performs scan at a second scan pitch ($P_L$) narrower than a first scan pitch ($P_H$) to capture the tomographic images of the subject's eye fundus. The image processing means compresses the picture (B11) of the tomographic images captured at the second scan pitch ($P_L$) in the scan direction to generate the new tomographic picture (B12). The measurement width in the scan direction of the (Continued)

new tomographic picture (B12) is a width of a picture corresponding to a measurement width in the scan direction of a tomographic picture (Bn (n=1 to 10)) obtained by scan at the first scan pitch ($P_H$).

9 Claims, 6 Drawing Sheets

(51) Int. Cl.
*A61B 3/00* (2006.01)
*G01B 9/02* (2006.01)

(52) U.S. Cl.
CPC .............. *A61B 3/1025* (2013.01); *A61B 3/14* (2013.01); *G01B 9/02091* (2013.01)

(58) Field of Classification Search
CPC .............. A61B 3/1025; G01B 9/02091; G01B 9/02055; G01B 9/02062
USPC .................... 351/205, 206; 348/78; 382/166
See application file for complete search history.

(56) References Cited

U.S. PATENT DOCUMENTS

| | | | |
|---|---|---|---|
| 2011/0134392 A1 | 6/2011 | Iwase et al. | 351/206 |
| 2011/0234786 A1 | 9/2011 | Yuasa et al. | 348/78 |
| 2012/0249953 A1 | 10/2012 | Ono | 351/206 |
| 2013/0173750 A1* | 7/2013 | Carnevale | G06F 19/321 |
| | | | 709/218 |
| 2013/0195340 A1 | 8/2013 | Iwase et al. | 382/131 |
| 2013/0222566 A1 | 8/2013 | Murase | 348/78 |
| 2013/0258283 A1 | 10/2013 | Goto et al. | 351/206 |
| 2014/0204338 A1 | 7/2014 | Murase et al. | 351/206 |
| 2015/0092161 A1* | 4/2015 | Akita | A61B 3/0025 |
| | | | 351/206 |
| 2016/0066785 A1* | 3/2016 | Gerrans | A61B 3/0083 |
| | | | 351/206 |

FOREIGN PATENT DOCUMENTS

| | | |
|---|---|---|
| JP | 2010188114 | 9/2010 |
| JP | 2012213465 | 11/2012 |
| JP | 2012249715 | 12/2012 |
| JP | 2013179971 | 9/2013 |
| JP | 2013179972 | 9/2013 |
| JP | 2014140488 | 8/2014 |
| WO | 2011122004 | 10/2011 |

OTHER PUBLICATIONS

Glenn J. Jaffe et al., "Optical Coherence Tomography to Detect and Manage Retinal Disease and Glaucoma", American Journal of Opthalmology, vol. 137, No. 1, pp. 156-169, Oct. 8, 2003 (Year: 2003).*
Maciej Wojtkowski et al., "Three-dimensional Retinal Imaging with High-Speed Ultrahigh-Resolution Optical Coherence Tomography", Opthalmology, 112(10), pp. 1734-1746, Oct. 2005 (Year: 2005).*
International Search Report dated May 17, 2016 in International Application No. PCT/JP2016/055750.
European Search Report dated Sep. 24, 2018 in Application No. 16 755 670.3.

* cited by examiner

[FIG. 1]
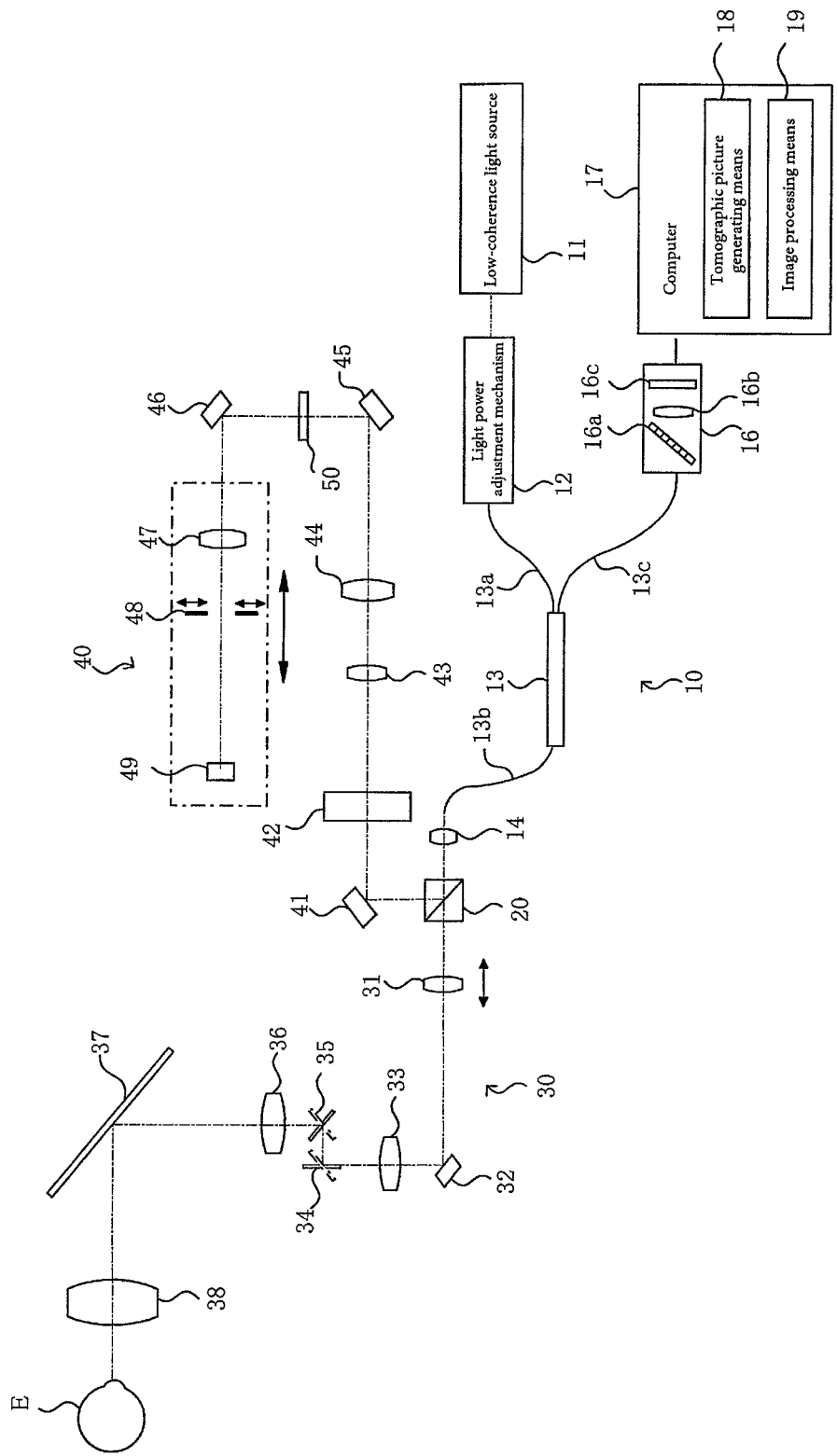

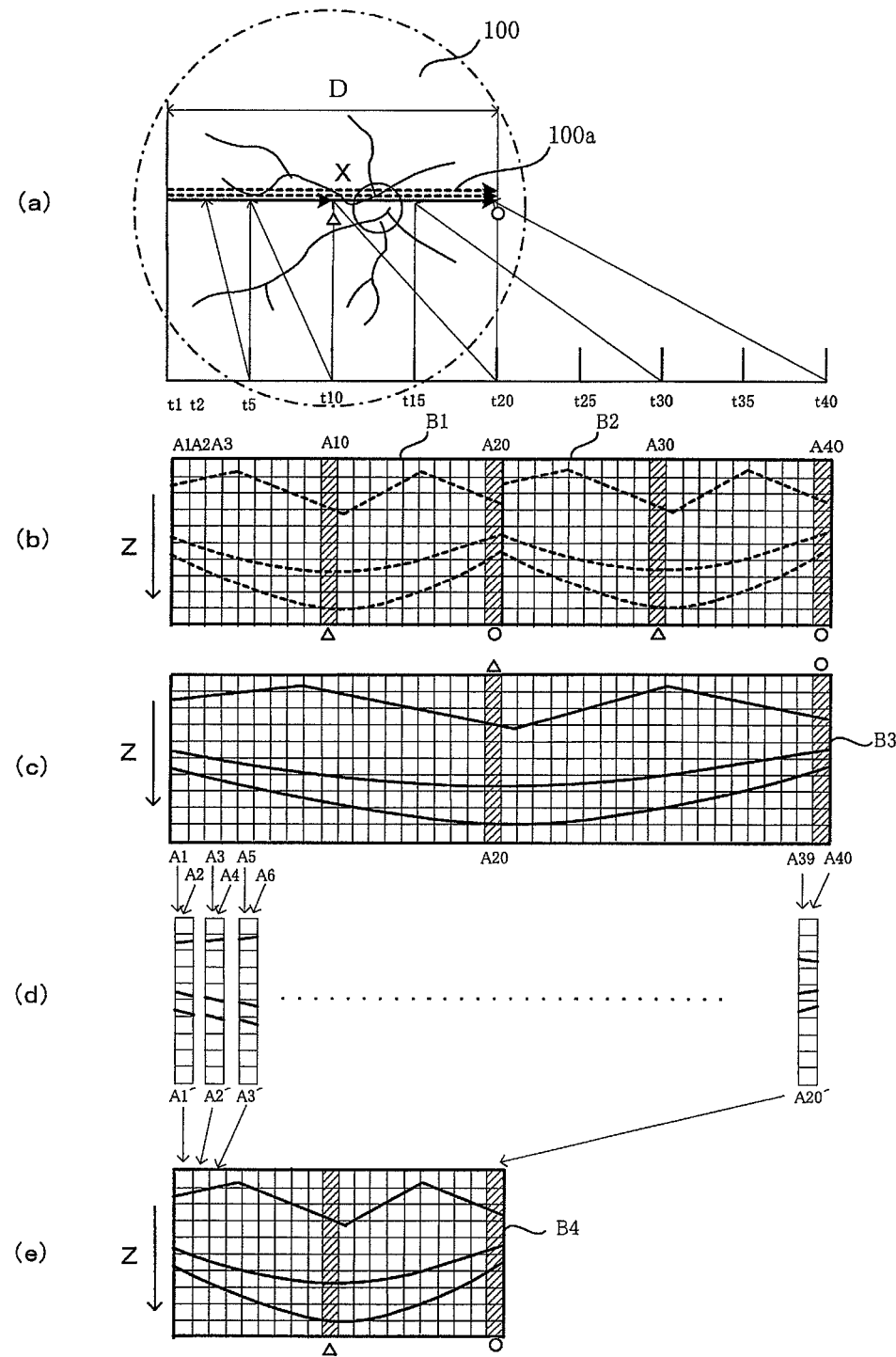
[FIG. 2]

[FIG. 3]
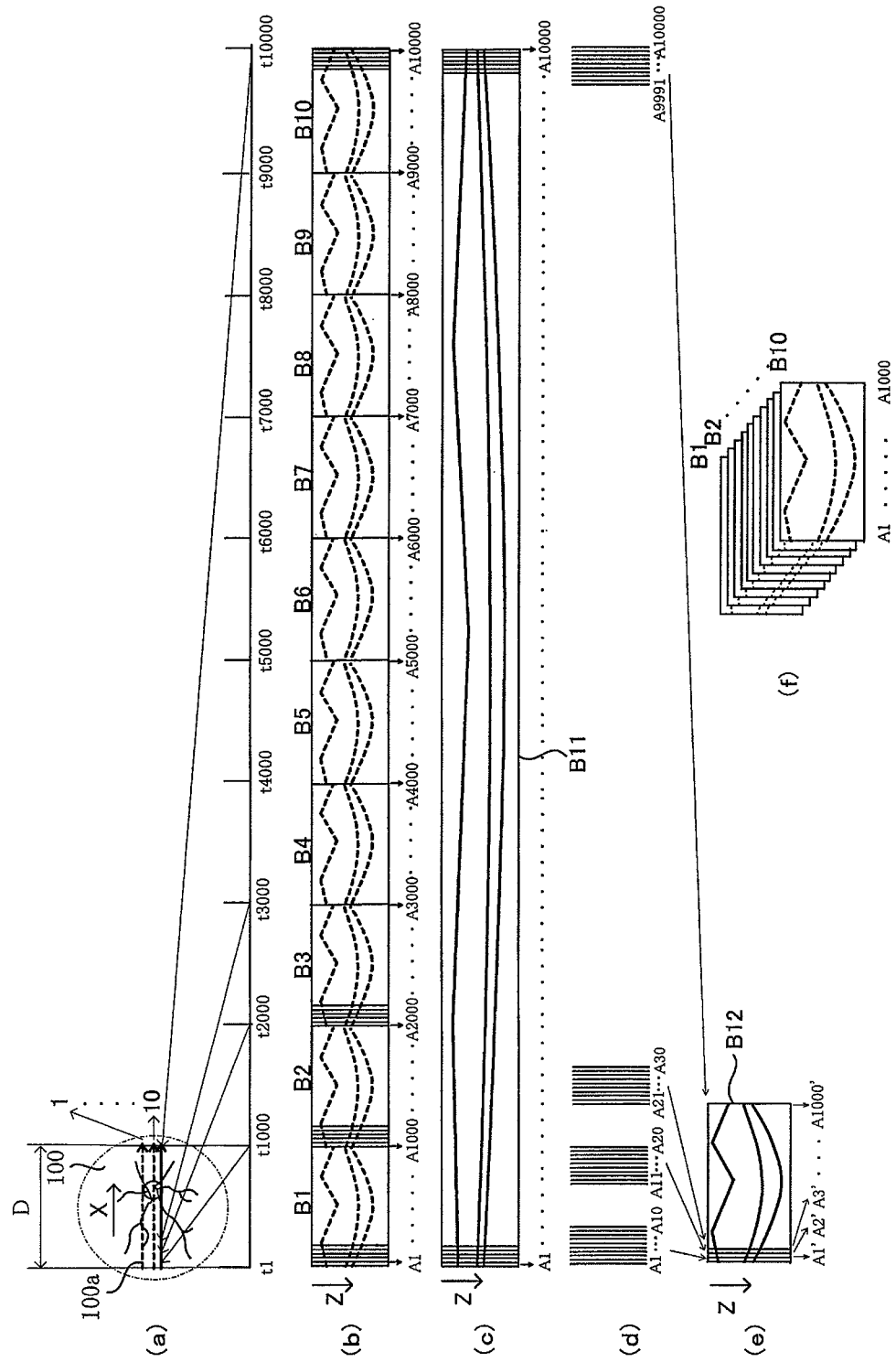

[FIG. 4]

| | Prior art | Present embodiment |
|---|---|---|
| Number of A scans | 1,000 * 10 | 10,000 * 1 |
| Necessary time for B scan(s) (ratio) | 1 | 10 |
| Number of adding processes | 10 | 10 |
| Time interval between samplings of A-scan pictures to be added | Long | Short |
| Variation of speckle | Large | Small |
| Effect of addition | Speckle is reduced | Speckle is emphasized |

[FIG. 5]
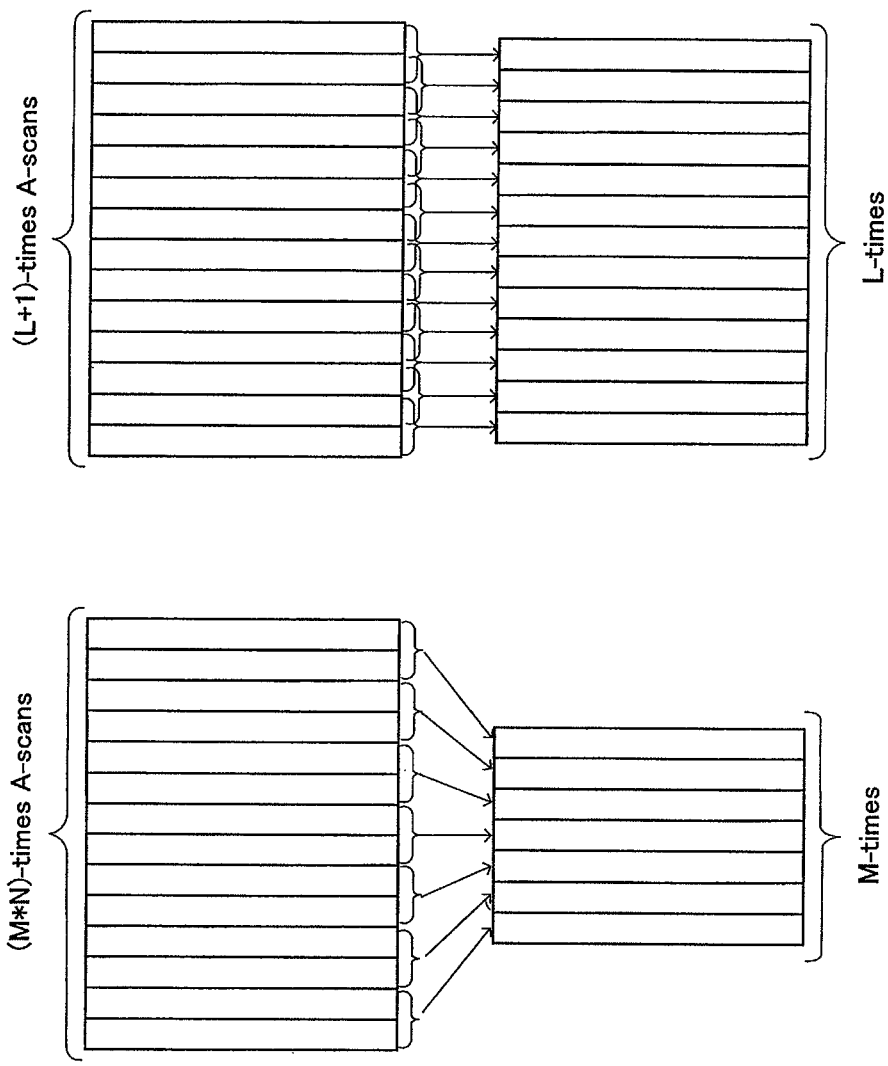

[FIG. 6]
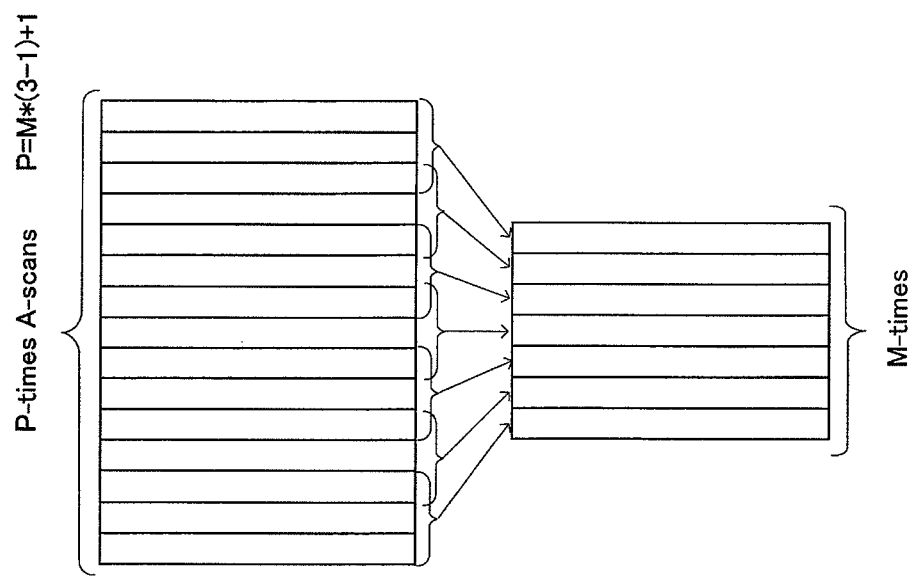

TOMOGRAPHIC IMAGE CAPTURING DEVICE

TECHNICAL FIELD

The present invention relates to a tomographic image capturing device that forms a tomographic picture of a target object on the basis of interference light generated by superposition of measurement light reflected from the target object and reference light reflected from a reference object.

BACKGROUND ART

As a type of ophthalmic diagnostic devices, tomographic image capturing devices are put into practical use, which utilize optical interference of so-called optical coherence tomography (OCT) to capture tomographic images of ocular fundus. When the horizontal direction, vertical direction, and depth of an ocular fundus are represented by x-direction, y-direction, and z-direction, respectively, such tomographic image capturing devices can acquire tomographic pictures (B-scan pictures) in the xz-direction. In ordinary image capture using the OCT, the tomographic images are captured, for example, at a rate of 40 images per second and a set of 100 or more tomographic pictures of a retina can be acquired by one-time testing (image capture at a part of the retina).

However, such tomographic pictures include a large amount of noise and the like and each raw picture is thus not suitable for tomographic interpretation. In this regard, various methods of image processing have been conventionally proposed to generate high-quality pictures suitable for tomographic interpretation. For example, an adding process is performed on pictures of a set of captured tomographic pictures to generate a picture for tomographic interpretation. Patent Literature 1 discloses a technique of adding and averaging the captured entire two-dimensional tomographic images to generate a tomographic picture with less noise.

To avoid distortion of tomographic pictures due to the effect of involuntary eye movements, high-speed measurement is needed as much as possible. Patent Literature 2 discloses a technique in which, to reduce the time necessary for the measurement, a measurement region is irradiated with a plurality of measurement light beams while being displaced by a small distance and scanned with the beams in the same direction and an adding and averaging process is performed on the obtained plurality of two-dimensional tomographic pictures to generate a tomographic picture with less noise.

PRIOR ART LITERATURE

Patent Literature

[Patent Literature 1] JP2008-237238A
[Patent Literature 2] JP2010-188114A

SUMMARY OF THE INVENTION

Problems to be Solved by the Invention

Even when a plurality of pictures is added and averaged to generate a high-quality picture suitable for tomographic interpretation as disclosed in Patent Literature 1 and Patent Literature 2, it is not possible to obtain a high-definition picture that is finer than the plurality of original pictures.

The present invention has been made in consideration of the above and an object of the present invention is to provide a tomographic image capturing device that can obtain a high-quality and high-density picture suitable for tomographic interpretation.

Means for Solving the Problems

To achieve the above object, the present invention provides a tomographic image capturing device comprising: a tomographic image capturing means that scans measurement light on a subject's eye fundus to capture tomographic images of the subject's eye fundus; and an image processing means that compresses a picture of the captured tomographic images in a scan direction to generate a new tomographic picture (Invention 1).

In a preferred embodiment of the above invention (Invention 1), the tomographic image capturing means may perform scan at a second scan pitch narrower than a first scan pitch to capture the tomographic images of the subject's eye fundus, the image processing means may compress the picture of the tomographic images captured at the second scan pitch in the scan direction to generate the new tomographic picture, and a measurement width in the scan direction of the new tomographic picture may be a width of a picture corresponding to a measurement width in the scan direction of a tomographic picture obtained by scan at the first scan pitch (Invention 2).

The picture of the tomographic images, which are obtained by scanning an image capturing target region of the subject's eye fundus at a higher scan density (narrower scan pitch, second scan pitch) than a predetermined scan pitch (first scan pitch), has a larger number of A-scan pictures that constitute the picture than in a picture of tomographic images obtained by scanning the same image capturing target region at the predetermined scan pitch (first scan pitch), and is a high-density tomographic picture. According to the above invention (Invention 2), when this high-density picture is compressed in the scan direction to generate a new tomographic picture, the new tomographic picture is generated such that the measurement width in the scan direction of the new tomographic picture is a measurement width corresponding to the measurement width in the scan direction of a tomographic picture that is obtained by scan at the predetermined scan pitch (first scan pitch), and a picture can thereby be obtained that is a tomographic picture having the same measurement width as that of the tomographic picture obtained by scan at the predetermined scan pitch (first scan pitch) but has a higher density than that of the tomographic picture obtained by scan at the predetermined scan pitch (first scan pitch).

Moreover, when the tomographic picture is newly obtained by compression in the scan direction as the above to have the same measurement width as that of the tomographic picture obtained by scan at the predetermined scan pitch, the speckle pattern, which may be regarded as noise and made to disappear if one picture for tomographic interpretation is obtained by adding and averaging a plurality of tomographic pictures obtained by scan at the predetermined scan pitch, is rather emphasized to appear in the new tomographic picture thus obtained. There can therefore be obtained a picture that is considerably effective when positively taking advantage of the speckle pattern to obtain information regarding the status of ocular fundus tissues in more detail from the tomographic picture.

In general, the term "compression" of a picture may be used to mean reducing the data capacity of the picture, but the compression as used in the present invention is not limited to such meaning and refers to a concept that encompasses reducing only the size of a picture in a specific direction, creating one picture from a plurality of pictures using an adding and average process, creating one picture from a plurality of pictures using a filtering process, and selecting one picture from among a plurality of pictures.

In a preferred embodiment of the above invention (Invention 2), the image processing means may compress every n pictures of A-scan pictures in the scan direction and combines the compressed A-scan pictures in the scan direction to generate the new tomographic picture, wherein the A-scan pictures constitute the picture of the tomographic images captured at the second scan pitch (Invention 3).

In the above invention (Invention 3), each of the compressed A-scan pictures may be generated by performing an adding and averaging process on n pictures of the A-scan pictures in the scan direction (Invention 4), or each of the compressed A-scan pictures may be generated by performing a filtering process on n pictures of the A-scan pictures (Invention 5).

In a preferred embodiment of the above invention (Invention 1 to 4), the second scan pitch may be 1/n of the first scan pitch (Invention 6).

Advantageous Effect of the Invention

According to the tomographic image capturing device of the present invention, a high-quality and high-density picture suitable for tomographic interpretation can be obtained.

BRIEF DESCRIPTION OF DRAWINGS

FIG. 1 is an optics view illustrating the overall configuration of a tomographic image capturing device according to an embodiment of the present invention.

FIG. 2 is an explanatory view illustrating a concept of high-density scan and picture compression carried out in the embodiment.

FIG. 3 is an explanatory view illustrating a concept of high-density scan and picture compression carried out in another embodiment.

FIG. 4 is an explanatory view for comparing a conventional method of obtaining a picture for tomographic interpretation by an adding and averaging process and a method of obtaining a picture for tomographic interpretation by high-density scan and picture compression according to the present invention.

FIG. 5 is a conceptual diagram for describing another embodiment of picture compression according to the present invention.

FIG. 6 is a conceptual diagram for describing another embodiment of picture compression according to the present invention.

EMBODIMENTS FOR CARRYING OUT THE INVENTION

Hereinafter, one or more embodiments of the present invention will be described in detail with reference to the drawings. As illustrated in FIG. 1, the tomographic image capturing device according to the present embodiment, which can be applied to an ocular fundus of a subject's eye E as the image capturing target object, is to capture tomographic images of a desired region of the ocular fundus by raster scan. The part denoted by reference numeral 10 is a demultiplexing/multiplexing optical system. This optical system may be provided with a broadband low-coherence light source 11 that comprises, for example, a super-luminescent diode (SLD) and emits light of a temporal coherence length of about several micrometers to several tens of micrometers at a wavelength of 700 nm to 1,100 nm.

The low-coherence light generated in the low-coherence light source 11 passes through a light power adjustment mechanism 12, in which the light power is adjusted, and is incident to an optical coupler 13 via an optical fiber 13a and then introduced into a beam splitter 20 as a splitting optical element via an optical fiber 13b and a collimator lens 14. In an alternative embodiment, demultiplexing and/or multiplexing may be performed using an optical circulator as substitute for the optical coupler 13.

The light incident to the beam splitter 20 is split into reference light and measurement light. The measurement light is incident to a focusing lens 31, which is to focus the measurement light on the ocular fundus of the subject's eye E. The measurement light to be focused on the ocular fundus is reflected by a mirror 32, passes through a lens 33, and is scanned in an arbitrary direction by an x-axis scanning mirror (galvanometer mirror) 34 and y-axis scanning mirror (galvanometer mirror) 35. The measurement light scanned by the x-axis and y-axis scanning mirrors 34 and 35 passes through a scanning lens 36, is reflected by a dichroic mirror 37, and then passes through an objective lens 38 to be incident to the ocular fundus, which is thus scanned by the measurement light in the x-direction and y-direction. The measurement light reflected by the ocular fundus tracks back the above path to return to the beam splitter 20.

In such an optical system, the focusing lens 31, mirror 32, lens 33, x-axis scanning mirror 34, y-axis scanning mirror 35, scanning lens 36, dichroic mirror 37 and objective lens 38, which are located downstream the beam splitter 20, may constitute a measurement optical system 30 of the tomographic image capturing device. This measurement optical system may be provided with optical components, such as mirrors and lenses, other than the illustrated optical components, but they are omitted for descriptive purposes.

On the other hand, the reference light split by the beam splitter 20 is reflected by a mirror 41 and then passes through a dispersion compensation glass for objective lens 42 and lenses 43 and 44. Thereafter, the reference light is reflected by a mirror 45 and passes through a subject's eye dispersion compensation glass 50 that compensates for the refractive index dispersion of the subject's eye E as the target object. Then, the reference light is reflected by a dichroic mirror 46, passes through a focusing lens 47 and variable aperture 48, and reaches a reference mirror 49. The variable aperture 48 may adjust the light power. To adjust the optical path length, the focusing lens 47, variable aperture 48 and reference mirror 49 can move in the optical axis direction in an integrated manner, as indicated by the two-way arrow in FIG. 1. The reference light reflected by the reference mirror 49 tracks back the above optical path to return to the beam splitter 20.

In such an optical system, the mirror 41, dispersion compensation glass for objective lens 42, lenses 43 and 44, mirror 45, subject's eye dispersion compensation glass 50, dichroic mirror 46, focusing lens 47 and reference mirror 49 may constitute a reference optical system 40 of the tomographic image capturing device. The reference mirror 49 may act as a reference object. This reference optical system may be provided with optical components, such as mirrors and lenses, other than the illustrated optical components, but they are omitted for descriptive purposes.

The measurement light and reference light returned to the beam splitter 20 are superposed with each other to be interference light, which passes through the collimator lens 14, optical fiber 13b and optical coupler 13 and is incident to a spectroscope 16 via an optical fiber 13c. The spectroscope 16 may have a diffraction grating 16a, imaging lens 16b, line sensor 16c, and other necessary components. The interference light is diffracted by the diffraction grating 16a into a spectrum in accordance with the wavelength of the low-coherence light and forms an image on the line sensor 16c by the imaging lens 16b.

Signals from the line sensor 16c may be subjected to signal processing, including Fourier transformation, performed by a tomographic picture generating means 18 that is realized using one or more CPUs and the like of a computer 17. This signal processing generates a depth signal that represents information in the depth direction (z-direction) of the ocular fundus. When scanning the ocular fundus, the interference light at each sampling time point allows the depth signal (A-scan picture) to be obtained at the sampling time point. Completion of one scan can therefore generate a two-dimensional tomographic picture (B-scan picture) that comprises Z-direction pictures (A-scan pictures) along the scan direction.

The computer 17 may not only serve as the tomographic picture generating means 18 which generates a two-dimensional tomographic picture, but also have a function as an image processing means 19 that compresses the generated tomographic picture in the scan direction to generate a new tomographic picture.

The description will now be directed to a flow of scanning the ocular fundus of the subject's eye E at a scan pitch narrower than a predetermined scan pitch to capture tomographic images of the ocular fundus of the subject's eye E, generating a tomographic picture from the tomographic images captured at the high scan density, and compressing the generated tomographic picture in the scan direction to generate a new tomographic picture. FIG. 2 is an explanatory view illustrating a concept of high-density scan and picture compression that are carried out in the present embodiment and schematically illustrates a process of acquiring a tomographic picture of an ocular fundus using high-density scan and performing image processing on the acquired tomographic picture. In FIG. 2 and FIG. 3, ocular fundus 100 may correspond to the ocular fundus of the subject's eye E of FIG. 1 and it is assumed that the y-axis scanning mirror 35 is fixed and the x-axis scanning mirror 34 scans the same location, when viewed in the Y-direction, of the ocular fundus in the X-direction (horizontal direction).

In FIG. 2, a predetermined region 100a of the ocular fundus 100 illustrated in part (a) may be scanned at a predetermined scan speed $S_H$ across a width D in the X-direction (horizontal direction) and scan lines are illustrated as dashed lines. The predetermined scan speed $S_H$ ordinarily refers to a standard speed at which the scan is performed with a scan line in the X-direction when capturing tomographic images of the ocular fundus. In the present embodiment, when the scan width D is 5 mm, the predetermined scan speed $S_R$ may be a speed at which the scan is performed with the scan line when scanning the width D for about 0.01 to 0.02 seconds. During the X-direction scan, a tomographic picture may be captured at each sampling time point ti (i=1, 2, 3, . . . ). This tomographic picture, which is called an A-scan picture, represents a Z-direction picture (depth direction picture) of the ocular fundus at a certain position of the scan line at each sampling time point. The scan pitch is defined as a difference in position on the retina between two adjacent A-scan pictures (i.e. a length of the difference in position in the B-scan direction). In the present embodiment, each A-scan picture may have a width of one pixel in the X-direction and a length of 10 pixels in the Z-direction. The width and length of each A-scan picture is merely illustrative and not limited to these examples.

Part (b) of FIG. 2 illustrates A-scan pictures A1, A2, . . . at sampling time points t1, t2, . . . acquired in the above manner and shaded areas represent an A-scan picture A10 at an ocular fundus position "Δ" of the scan line at sampling time point t10 and an A-scan picture A20 at an ocular fundus position "○" of the scan line at sampling time point t20. Each of the acquired A-scan pictures may be stored in a storage part (not illustrated) of the computer 17 so as to be associated with corresponding pixels.

The X-direction scan may be completed at the sampling time point t20. Accordingly, the same location may be scanned again from the initial position. In part (a) of FIG. 2, the second-stage scan line is shifted from the first-stage scan line in the vertical direction, but this is for the descriptive purposes, and these scan lines are actually overlapped with each other.

In the second-stage scan line, A-scan pictures A21 to A40 obtained by scanning the same location as acquired at the sampling time points t1 to t20 may be acquired at sampling time points t21 to t40 and stored in the storage part of the computer 17. The A-scan pictures A1 to A20 may represent a tomographic picture of the ocular fundus across the X-direction width D. The picture comprising the A-scan pictures A1 to A20 is also referred to as a B-scan picture. In addition, a B-scan picture B2 of the same location as that of the B-scan picture B1 comprising the A-scan pictures A1 to A20 may be acquired from the A-scan pictures A21 to A40. Two frames of the tomographic pictures B1 and B2 represented by dashed lines may be stored in the storage part of the computer 17.

In the present embodiment, the same ocular fundus region 100a may be scanned with a scan line at a narrower scan pitch $P_L$ than a predetermined scan pitch $P_H$ that is for the scan lines represented by the dashed lines. This scan line is illustrated as a solid line in FIG. 2. Since the same location of the ocular fundus is scanned with each scan line in the X-direction, these scan lines should be illustrated as overlapped lines, but are illustrated as being shifted in the vertical direction for descriptive purposes.

The scan line illustrated as the solid line may have a scan pitch that is, for example, 1/n (n is integer larger than 1) of the scan pitch for the scan lines illustrated as dashed lines, and the integer n is two (n=2) in FIG. 2. The ocular fundus region 100a may therefore be scanned in the X-direction at a narrower scan pitch than the scan pitch $P_H$ by half, that is, at the scan pitch $P_L$ which is a pitch half the scan pitch $P_H$.

Since the ocular fundus region 100a is scanned at the narrow scan pitch $P_L$, the ocular fundus position for the scan line at each sampling time point ti may be located, in the horizontal direction, at a distance half the distance corresponding to the ocular fundus position for a scan line at the sampling time point ti when scanned with the scan line at the predetermined scan pitch $P_H$ (at a width twice the narrow scan pitch $P_L$ in FIG. 2), and the ocular fundus can thus be finely scanned in the X-direction at the half pitch of high density. Here, the scan at the narrow pitch of high density may be B-scan of a low speed ($S_L$), which is performed at a speed half the predetermined scan speed $S_H$, while the scan at the predetermined scan pitch may be B-scan of a high speed ($S_H$), which is performed at a speed twice the low speed ($S_L$). Thus, at the sampling time point t8, for example, the scan line of low speed $S_L$ may sample the ocular fundus position which the scan line of double speed $S_H$ scans at the sampling time point t4, and the A-scan picture A8 at that time point may be acquired. At the sampling time point t9, the scan line of low speed $S_L$ may sample the ocular fundus position which the scan line of double speed $S_H$ scans at the intermediate time point between the sampling time points t4 and t5, and the A-scan picture A9 at that time point may be acquired. At the sampling time point t10, the scan line of low speed $S_L$ may sample the ocular fundus position which the scan line of double speed $S_H$ scans at the sampling time point t5, and the A-scan picture A10 at that time point may be acquired. Likewise, scan pictures A11 to A20 may be each acquired by sampling the ocular fundus position which the scan line of double speed $S_H$ scans at the intermediate time point between each sampling time point and next sampling time point. The scan line of low speed $S_L$ scans only half the width D to be scanned, even at the sampling time point t20, and may therefore sample the remaining half during the period from the sampling time point t21 to the sampling time point t40, and a B-scan picture B3 comprising the A-scan pictures A1 to A40 can be obtained as illustrated in part (c) of FIG. 2.

Thus, the X-direction width D as the image capturing target may be scanned at the scan pitch $P_L$ to obtain a B-scan picture. Again, the scan pitch $P_L$ is a scan pitch of a width half the predetermined scan pitch $P_H$. The number (40) of A-scan pictures that constitute the above B-scan picture is therefore larger than the number (20) of A-scan pictures that constitute a B-scan picture obtained by scanning the same X-direction width D at the predetermined scan pitch $P_H$. In other words, image capture of the same location at the half scan pitch means image capture at the low speed (i.e. half speed), or means sampling of the ocular fundus position at a scan pitch of the predetermined pitch, that is, sampling of the ocular fundus position at the intermediate time point between each sampling time point and next sampling time point for the double-speed scan line. Thus, the ocular fundus may be finely and highly densely scanned with the double sampling number and a tomographic picture of high definition can therefore be obtained accordingly. It should be noted, however, that the measurement width (one pixel) of A-scan pictures that constitute each tomographic picture is fixed and the B-scan picture B3 obtained as the above is therefore expanded in the X-direction. That is, within the range corresponding to the width D on the retina, the number of pixels in the total width of the B-scan picture B3 is twice the number of pixels of each of the B-scan pictures B1 and B2.

The B-scan picture B3 acquired with the scan pitch $P_L$ of high density may be compressed in the X-direction as illustrated in part (e) of FIG. 2 and a new B-scan picture B4 may be generated. In order to compress the B-scan picture, which is acquired with the scan pitch $P_L$ having a width that is 1/n of the predetermined scan pitch $P_H$, in the scan direction (X-direction), every n pictures of A-scan pictures may be compressed in the scan direction and the compressed A-scan pictures may be combined in the scan direction to generate a new tomographic picture. In the present embodiment, the scan pitch being half allows the number of A-scan pictures, which constitute the B-scan picture B3, to be twice and, therefore, every two pictures of the A-scan pictures A1 to A40 which constitute the B-scan picture B3 may be compressed in the X-direction.

Specifically, as illustrated in part (d) of FIG. 2, each pixel of the A-scan picture A1 and each pixel of the A-scan picture A2 may be added and averaged in the X-direction to generate a new A-scan picture A1'. Likewise, the A-scan pictures A3 and A4, the A-scan pictures A5 and A6, ..., and the A-scan pictures A39 and A40 may be added and averaged to respectively generate new A-scan pictures A2', A3', ..., and A20'. Then, the A-scan pictures A1' to A20' created in this manner may be combined in the X-direction to generate the B-scan picture B4, as illustrated in part (e) of FIG. 2, which represents respective pixels of the B-scan pictures B1 and B2.

In the present embodiment, two A-scan pictures are added and averaged in the scan direction to generate one new A-scan picture. In an alternative embodiment, for example, a filtering process may be performed on two A-scan pictures to generate one new A-scan picture. Possible examples of the filtering process include a moving average process and a median process. In addition or alternatively, a compression process may be performed, such as by performing a filtering process on two A-scan pictures and then adding them.

The picture width in the X-direction of the B-scan picture B4 compressed in the horizontal direction as the above is the same as the picture width of each of the B-scan pictures B1 and B2 which are obtained by the scan at the predetermined pitch width $P_H$. Fortunately, however, each pixel of the B-scan picture B4 records a fine part of the ocular fundus because the B-scan picture B4 is obtained by adding and averaging pixels of the B-scan picture B3 of high density in the horizontal direction. Accordingly, the average of respective pixels also represents an average value of fine parts. The B-scan picture B4 is therefore a picture (high-definition picture) that is excellent in the reproducibility of fine parts as compared with the B-scan pictures B1 and B2.

The B-scan picture B4 obtained as described above is a high-definition picture as compared with the B-scan pictures B1 and B2 and, in the B-scan picture B4, a speckle pattern is emphasized to appear. The B-scan picture B4 is therefore considerably effective when positively taking advantage of the speckle pattern to obtain information regarding the status of ocular fundus tissues in more detail from the tomographic picture. The speckle pattern as referred to herein is a picture pattern based on a phenomenon that portions of high intensity and low intensity of scattered light occur due to an indefinitely large number of superpositions of scattered light from a scattering body in the measurement target. The speckle pattern itself does not directly represent the structure of an ocular fundus as the measurement target, but is recognized to vary in the appearance in accordance with the status of the ocular fundus. For this reason, studies are conducted to positively take advantage of statistical properties of the speckle pattern, rather than merely regarding the speckle pattern as noise.

If a plurality of B-scan pictures is merely added and averaged to generate a picture with less noise for tomographic interpretation as in the prior art, the speckle pattern will disappear. When, however, the compression is performed in the scan direction to generate a picture for tomographic interpretation as in the present embodiment, the speckle pattern is emphasized to appear. This may be due to the following reasons.

In the high-density scan, the time interval between samplings of targets to be added is very short and the scan speed is low, so that the distance of spatial movement during the sampling time period may also be short. The speckle pattern may therefore scarcely vary during the sampling and a high-contrast speckle signal can be observed. In the low-density scan, however, the spatial distance of movement during the sampling time period is long because the scan speed is high. During this period, the speckle pattern may vary. The average value of the varying speckle pattern is therefore to be sampled and the contrast of the speckle may be low. In addition, the speckle pattern may vary remarkably also due to the positional shift by the involuntary eye movements because the time interval between samplings of targets to be added is long. For these reasons, the contrast of the speckle may deteriorate more and more in the picture after the adding and averaging process.

For example, if the B-scan pictures B1 and B2 illustrated in FIG. 2 are added and averaged to create a picture for tomographic interpretation, then, on the assumption that there is no positional shift, the adding and averaging process is performed on the A-scan picture A1 of the B-scan picture B1 and the A-scan picture A21 of the B-scan picture B2, on the A-scan picture A2 of the B-scan picture B1 and the A-scan picture A22 of the B-scan picture B2, . . . , and on the A-scan picture A20 of the B-scan picture B1 and the A-scan picture A40 of the B-scan picture B2.

Here, the interval between the sampling time point t1 for the A-scan picture A1 of the B-scan picture B1 and the sampling time point t21 for the A-scan picture A21 of the B-scan picture B2 corresponds to one scan. If the speckle pattern varies due to involuntary eye movements during that interval corresponding to one scan, the speckle pattern will disappear in the same way as other noises when the A-scan pictures A1 and A2 are added and averaged, and only the tomographic structure may remain. The possibility that the speckle pattern varies due to involuntary eye movements may become higher as the time interval between samplings of A-scan pictures to be added and averaged increases (as the time difference increases between when one picture is obtained and when the other picture is obtained).

In contrast, in the present embodiment, two adjacent A-scan pictures may be added and averaged to create a new A-scan picture and such new A-scan pictures may be combined to obtain the new B-scan picture B4 through the compression performed such that the total width of the B-scan picture B3 of which the measurement width is twice the measurement width of each of the B-scan pictures B1 and B2 can be approximately the same as the total width of each of the B-scan pictures B1 and B2. In this compression, two A-scan pictures to be added and averaged are successively sampled. More specifically, the A-scan pictures A1 and A2 are successively sampled, the A-scan pictures A3 and A4 are successively sampled, and so on. The time interval between samplings of two A-scan pictures (the time difference between when one picture is obtained and when the other picture is obtained) is therefore very short. In this case, the possibility may be high that the speckle pattern does not vary due to involuntary eye movements and a substantially similar speckle pattern occurs, for example, between the A-scan pictures A1 and A2. The speckle pattern may therefore not disappear even after the adding and averaging process while other noises disappear. Rather, the speckle pattern may be emphasized to appear.

Next, a process illustrated in FIG. 3 (n=10) will be described. This process may include acquiring tomographic pictures by high-density scan at a narrower pitch that is ⅒ of a predetermined scan pitch and performing image processing on the acquired tomographic pictures. The configuration of the tomographic image capturing device is just the same and the procedure is almost the same as the previous embodiment, so redundant description will not be repeated.

In the present embodiment, a predetermined region 100a of an ocular fundus 100 illustrated in part (a) of FIG. 3 may be scanned at a predetermined scan pitch $P_H$ across a width D in the X-direction (horizontal direction). One scan at the predetermined scan pitch $P_H$ may include 1000 samplings. In this case, as illustrated in part (b) of FIG. 3, created B-scan pictures include a B-scan picture B1 comprising 1000 A-scan pictures A1, . . . , A1000, a B-scan picture B2 comprising 1000 A-scan pictures A1001, . . . , A2000, . . . , and a B-scan picture B10 comprising 1000 A-scan pictures A9001, . . . , A10000. There are therefore sampling time points represented by ti (i=1 to 10000), and the generated B-scan pictures B1 to B10 are pictures at the same location. Thus, as illustrated in part (f) of FIG. 3, B-scan pictures of 10 frames (10 sheets) are acquired.

Here, the scan at a narrow pitch of high density may be scan of a low speed $S_L$, which is performed at a speed that is apparently ⅒ of a predetermined scan speed, while the scan at the predetermined scan speed may be scan of a high speed $S_H$, which is performed at a speed 10 times the low speed. Since the low scan speed $S_L$ is ⅒ of the predetermined scan speed $S_H$, the scan line of low scan speed $S_L$ may sample ocular fundus portions, which are located at respective positions obtained by equally dividing the scanning distance for the scan line of scan speed $S_H$ between sampling time point t(i) and sampling time point t(i+1) into 10 segments, at 10 sampling time points of t(10i+1), t(10i+2), t(10i+9), and t(10i+10). In the scan of scan speed $S_L$ which is ⅒ of the scan speed $S_S$, therefore, positions of 10 sites between adjacent sampling time points for the scan line of scan speed $S_H$ are finely and highly densely sampled, and the number of A-scan pictures obtained by the scan of scan speed $S_L$ which is ⅒ of the scan speed $S_H$ may be 10 times the number of A-scan pictures obtained by the scan of scan speed $S_H$ for each B-scan picture. Thus, the low-speed scan may be performed for samplings at the sampling time points t1, t10000 as illustrated in part (a) of FIG. 3, and a B-scan picture B11 can thereby be created as illustrated in part (c) of FIG. 3. The B-scan picture B11 is composed of 10000 A-scan pictures A1 to A10000. Again, the number of the A-scan pictures A1 to A10000 is 10 times the number of A-scan pictures obtained at the speed $S_H$ for each B-scan picture. The total width of the B-scan picture B11 is 10 times the total width of each of the B-scan pictures B1, B2, . . . , B10.

The B-scan picture B11 acquired with the narrow scan pitch $P_L$ may be compressed in the X-direction as illustrated in part (e) of FIG. 3 and a new B-scan picture B12 may be generated. In the present embodiment, the scan pitch being ⅒ allows the number of A-scan pictures, which constitute the B-scan picture B11, to be 10 times and, therefore, every 10 pictures of the A-scan pictures may be compressed in the X-direction. Specifically, for 10 contiguous A-scan pictures, that is, for the A-scan pictures A1 to A10, A11 to A20, A21 to A30, . . . , and A9991 to A10000, respective pixels of the A-scan pictures may be added and averaged in the X-direction, as illustrated in part (d) of FIG. 3, to create 1000 new A-scan pictures A1', A2', . . . , and A1000', and these 1000 A-scan pictures may be combined in the X-direction to generate a new B-scan picture 12 of which the total width corresponds to the total width of each of the B-scan pictures B1 to B10.

FIG. 4 illustrates general comparison between a case as in the present embodiment in which the B-scan picture B11 obtained by high-density scan with the narrow scan pitch $P_L$ is compressed in the scan direction to generate the new B-scan picture B12 for tomographic interpretation and a case as in the prior art in which a plurality of B-scan pictures B1, B2, . . . , and B10 (10 pictures) obtained by scan with the predetermined scan pitch $P_H$ is added and averaged to create one picture for tomographic interpretation.

When the adding and averaging process is performed on 10 pictures of B-scan pictures as in the prior art, the number of A-scans (samplings) is 1000 for one B-scan picture, that is, 10000 in total for 10 pictures. When the B-scan picture obtained by high-density scan is compressed in the scan direction as in the present embodiment, the number of A-scans is also 10000. To generate one B-scan picture, the present embodiment may require a time 10 times longer than the prior art in general, but the total time is the same because 10 pictures of B-scan pictures are acquired in the prior art. The number of adding processes for obtaining each A-scan picture that constitutes a picture for tomographic interpretation is 10, which is also the same in the present embodiment and in the prior art.

However, when the adding and averaging process is performed on 10 pictures of the B-scan pictures as in the prior art, the time interval between samplings of A-scan pictures to be added (the time difference between when a picture is obtained and when the corresponding picture is obtained) corresponds to a time required for one scan, while in contrast, when the B-scan picture obtained by high-density scan is compressed in the scan direction as in the present embodiment, 10 pictures of the A-scan pictures which are successively sampled are added. As the time interval between samplings of pictures increases (as the time difference increases between when a picture is obtained and when the corresponding picture is obtained), the speckle pattern largely varies. In the prior art, therefore, the speckle pattern is reduced by the adding and averaging process while, in the present embodiment, the speckle pattern is emphasized by the adding and averaging process.

When the high-density scan is performed as in the present embodiment, the time required for one scan is longer as compared with the prior art and it may therefore be necessary to contrive a method for responding to the problem of involuntary eye movements of the subject's eye during such a long time required for one scan. This will be specifically described. When the adding and averaging process is performed on 10 pictures of B-scan pictures in the prior art, the influence of involuntary eye movements appears as the positional shift of each picture. On the other hand, in the present embodiment, the influence of involuntary eye movements appears as distortion in the B-scan picture. Using a picture with such distortion may problematic in tomographic interpretation and it is thus desired to appropriately correct the distortion. One such method for correction is to perform correction using an ideal tomographic reference model that is estimated from information on the diopter scale of a subject's eye. When this method is employed, however, the possibility cannot be denied that the situation of the shape specific to the subject's eye may be erroneously determined. In the present embodiment, therefore, a method may be employed which includes performing high-speed scan at the same location as that for high-density scan thereby to acquire a picture with low possibility of generation of distortion (referred to as a "reference picture," hereinafter) and correcting the distortion of a tomographic picture obtained by the high-density scan using the reference picture. The high-speed scan may be performed once or a few times before and/or after performing the high-density scan.

The process of acquiring the reference picture will be referred to as an "alignment scan," hereinafter. The scan pitch for the alignment scan may be the previously-described first scan pitch, but the situation is that the tomographic picture should be acquired in a short time, so the scan pitch may also be a scan pitch as in a so-called draft scan in which the tomographic picture is acquired with a wider scan pitch than the first scan pitch. As will be understood, the high-density scan may be performed at the second scan pitch as previously described.

The reference picture for alignment may be required to have a more correct structural feature of the scanning site, but, as previously described, even when the same site is scanned, the structure of a tomographic picture obtained in an ocular fixation state (state of involuntary eye movements) may exhibit a different form in each scan. In the present embodiment, therefore, the reference picture for alignment may be created from a tomographic image such that the possibility can be highest that the reference picture is captured to be approximately the same as the high-density tomographic picture (i.e., the same location on a subject's eye is scanned). The tomographic image may be obtained by the alignment scan immediately before the high-density scan. In this case, when the alignment scan is performed once, the one picture obtained may be employed as the reference picture, or when the alignment scan is performed twice or more, the latest one of the set of tomographic pictures obtained may be employed as the reference picture. Other possible examples of methods of determining the reference picture include various variations, such as selecting a picture having highest correlation from among a set of tomographic pictures, employing a simple average picture of a set of tomographic pictures, determining an average picture that is aligned with a set of tomographic pictures, and determining an average picture that is aligned with reference to a picture having highest correlation among a set of tomographic pictures.

After executing the alignment scan to acquire the reference picture and executing the high-density scan to acquire a high-definition tomographic picture, alignment between the reference picture and the high-definition tomographic picture may be performed. Various methods can be employed as methods for this alignment. A first possible example is to carry out the alignment on the basis of the same one or more boundary segmentation lines among segmentation lines. A second possible example is to carry out the alignment on the basis of strong and weak patterns of the tomographic picture obtained due to the vessel structure. In this example, magnification correction and correction of ununiform scan speed in the scan direction (vertical direction) are possible. A third possible example is to carry out the alignment on the basis of correlation of the same one or more pictures.

Thus, by performing the alignment between the reference picture obtained by the alignment scan and the tomographic picture obtained by the high-density scan, the influence of involuntary eye movements caused during the high-density scan can be suppressed as much as possible.

The alignment scan can be omitted, such as during the retest, if image capture of the same site of the same subject's eye is preliminarily performed. In this case, the reproducibility in image capture of the same site may have to be ensured, such as using a follow-up function, but a tomographic picture of the same site which is preliminarily captured in a separate procedure can be employed as the reference picture. In an alternative embodiment, if it is recognized that the structural change of the retina structure does not occur and/or the feature amount used for alignment does not vary, it is possible to apply the tomographic picture of the same site which has already been captured or which will be captured in the future using a follow-up function.

Thus, according to the tomographic image capturing device of the present embodiment, a high-quality and high-definition picture for tomographic interpretation can be obtained. Moreover, when the tomographic picture is newly obtained by compression in the scan direction as the above to have the same measurement width as that of the tomographic picture obtained by scan at the predetermined scan speed, the speckle pattern, which may be regarded as noise and made to disappear if one picture for tomographic interpretation is obtained by adding and averaging a plurality of tomographic pictures obtained by scan at the predetermined scan speed, is rather emphasized to appear in the new tomographic picture thus obtained. There can therefore be obtained a picture that is considerably effective when positively taking advantage of the speckle pattern to obtain information regarding the status of ocular fundus tissues in more detail from the tomographic picture. Furthermore, the distortion of a tomographic picture, which may be caused by the influence of involuntary eye movements during acquisition of the picture in the high-density scan, can be corrected by utilizing a tomographic picture or the like obtained in a higher-speed scan (at a wider scan pitch) before or after the distortion occurs.

The tomographic image capturing device according to the present invention has been described hereinbefore with reference to the drawings, but the present invention is not limited to the above embodiments and various modified embodiments are possible.

For example, in the above-described embodiment, when scan is performed at a scan pitch that is 1/n of the original scan pitch, the B-scan picture obtained by the high-density scan is compressed to 1/n of the original picture in the scan direction, but the multiplier n of the scan pitch and the multiplier n at the time of compression may be different. For example, for a B-scan picture obtained at a pitch that is 1/10 of the original pitch, a compressed new B-scan picture may be generated by adding and averaging every 8 or 9 contiguous pictures of the A-scan pictures rather than adding and averaging every 10 contiguous pictures of the A-scan pictures. Depending on the value of n at the time of compression, the width on the retina corresponding to one pixel of the compressed B-scan picture in the scan direction may be different from the measurement width of the B-scan picture obtained by scan at the predetermined pitch. Even in such a case, provided that the widths of pictures corresponding to the measurement widths of both the B-scan pictures are not significantly different and they are practically corresponding values, the multiplier n of the scan pitch and the multiplier n at the time of compression may be different. In this case, the same A-scan picture may be used for calculation in an overlapped manner. FIG. 5 and FIG. 6 are conceptual diagrams of these embodiments.

For example, the left-side example of FIG. 5 illustrates a case in which, as heretofore described, the multiplier n of the scan pitch and the multiplier n at the time of compression are the same, while the right-side example illustrates a case in which the number of samplings is larger by one than the number L of samplings when scan is performed at the predetermined pitch. In the latter case, a compressed new B-scan picture may be generated by sequentially adding and averaging two adjacent A-scan pictures in an overlapped manner (i.e., for j=1 to L, adding and averaging j-th A-scan picture and (j+1)-th A-scan picture, then adding and averaging (j+1)-th A-scan picture and, (j+2)-th A-scan picture, and so on). In the example of FIG. 6, every three contiguous pictures of A-scan pictures are added and averaged for a B-scan picture comprising P pictures that are scanned and sampled at a predetermined pitch. More specifically, for J=1 to P, j-th A-scan picture, (j+1)-th A-scan picture, and (j+2)-th A-scan picture are added and averaged, then (j+2)-th A-scan picture, (j+3)-th A-scan picture, and (j+4)-th A-scan picture are added and averaged, and so on. That is, the adding and averaging process is performed such that the last A-scan picture of three A-scan pictures in the scan direction is also used in the subsequent set of three A-scan pictures in an overlapped manner.

DESCRIPTION OF REFERENCE NUMERALS

E Subject's eye
10 Demultiplexing/multiplexing optical system
11 Low-coherence light source
12 Light power adjustment mechanism
13 Optical coupler
14 Collimator lens
16 Spectroscope
17 Computer
18 Tomographic picture generating means
19 Image processing means
20 Beam splitter
30 Measurement optical system
31 Focusing lens
34 X-axis scanning mirror
35 Y-axis scanning mirror
36 Scanning lens
37 Dichroic mirror
38 Objective lens
40 Reference optical system
42 Dispersion compensation glass for objective lens
46 Dichroic mirror
47 Focusing lens
48 Variable aperture
49 Reference mirror
50 Subject's eye dispersion compensation glass

The invention claimed is:

1. A tomographic image capturing device comprising:
a tomographic image capturing means that scans measurement light on a subject's eye fundus to capture tomographic images of the subject's eye fundus; and
an image processing means that compresses a picture of the captured tomographic images in a scan direction to generate a new tomographic picture.

2. The tomographic image capturing device as recited in claim 1, wherein
the tomographic image capturing means performs scan at a second scan pitch narrower than a first scan pitch to capture the tomographic images of the subject's eye fundus,
the image processing means compresses the picture of the tomographic images captured at the second scan pitch in the scan direction to generate the new tomographic picture, and
a measurement width in the scan direction of the new tomographic picture is a width of a picture corresponding to a measurement width in the scan direction of a tomographic picture obtained by scan at the first scan pitch.

3. The tomographic image capturing device as recited in claim 2, wherein the image processing means compresses every n pictures of A-scan pictures in the scan direction and combines the compressed A-scan pictures in the scan direction to generate the new tomographic picture, wherein the A-scan pictures constitute the picture of the tomographic images captured at the second scan pitch.

4. The tomographic image capturing device as recited in claim 3, wherein each of the compressed A-scan pictures is generated by performing an adding and averaging process on n pictures of the A-scan pictures in the scan direction.

5. The tomographic image capturing device as recited in claim 3, wherein each of the compressed A-scan pictures is generated by performing a filtering process on n pictures of the A-scan pictures.

6. The tomographic image capturing device as recited in claim 5, wherein the second scan pitch is 1/n of the first scan pitch.

7. The tomographic image capturing device as recited in claim 4, wherein the second scan pitch is 1/n of the first scan pitch.

8. The tomographic image capturing device as recited in claim 3, wherein the second scan pitch is 1/n of the first scan pitch.

9. The tomographic image capturing device as recited in claim 2, wherein the second scan pitch is 1/n of the first scan pitch.

* * * * *